(12) United States Patent
Clarke et al.

(10) Patent No.: US 7,199,153 B2
(45) Date of Patent: Apr. 3, 2007

(54) PHARMACEUTICAL COMPOSITION COMPRISING PARACETAMOL AND NIFLUMIC ACID

(75) Inventors: Geoffrey Douglas Clarke, Weybridge (GB); Melanie Jayne Sammons, Harlow (GB); Mark Wyles, Harlow (GB)

(73) Assignee: SmithKline Beechman, p.l.c., Brentford (GB)

( * ) Notice: Subject to any disclaimer, the term of this patent is extended or adjusted under 35 U.S.C. 154(b) by 0 days.

(21) Appl. No.: 10/239,342

(22) PCT Filed: Mar. 20, 2001

(86) PCT No.: PCT/EP01/03185

§ 371 (c)(1),
(2), (4) Date: Jun. 6, 2003

(87) PCT Pub. No.: WO01/70205

PCT Pub. Date: Sep. 27, 2001

(65) Prior Publication Data

US 2004/0010044 A1 Jan. 15, 2004

(30) Foreign Application Priority Data

Mar. 23, 2000 (GB) ................. 0006897.3

(51) Int. Cl.
*A61K 31/34* (2006.01)
*A61K 31/16* (2006.01)

(52) U.S. Cl. .................... 514/474; 514/629
(58) Field of Classification Search ........... 514/474, 514/629
See application file for complete search history.

(56) References Cited

U.S. PATENT DOCUMENTS

| 4,097,606 | A | * | 6/1978 | Chavkin et al. | ............ 514/629 |
| 4,447,443 | A | * | 5/1984 | Goldenberg | ................ 514/400 |
| 4,595,686 | A | * | 6/1986 | Bru-Magniez et al. | ... 514/237.2 |
| 4,600,579 | A | * | 7/1986 | Salpekar et al. | ............ 514/629 |
| 4,748,174 | A | * | 5/1988 | Veronesi | ................ 514/226.5 |
| 6,028,222 | A | * | 2/2000 | Dietlin et al. | ................. 564/4 |
| 6,316,025 | B1 | * | 11/2001 | Grattan | ...................... 424/451 |

FOREIGN PATENT DOCUMENTS

| WO | WO 85/04589 | | 10/1985 |
| WO | WO 85/04589 A1 | * | 10/1985 |
| WO | WO 99/66919 | | 12/1999 |

OTHER PUBLICATIONS

Moreau X, et al. "Perioperative analgesia in the surgery of peripheral venins", Cahiers D Anesthesiologie, Dec. 1990, 38(6), pp. 403-407.

* cited by examiner

*Primary Examiner*—Brian Kwon
(74) *Attorney, Agent, or Firm*—Dara L. Dinner; Theodore R. Furman; Charles M. Kinzig

(57) ABSTRACT

A formulation is described comprising paracetamol, niflumic acid or a pharmaceutically acceptable salt or ester thereof and a pharmaceutically acceptable excipient.

2 Claims, 6 Drawing Sheets

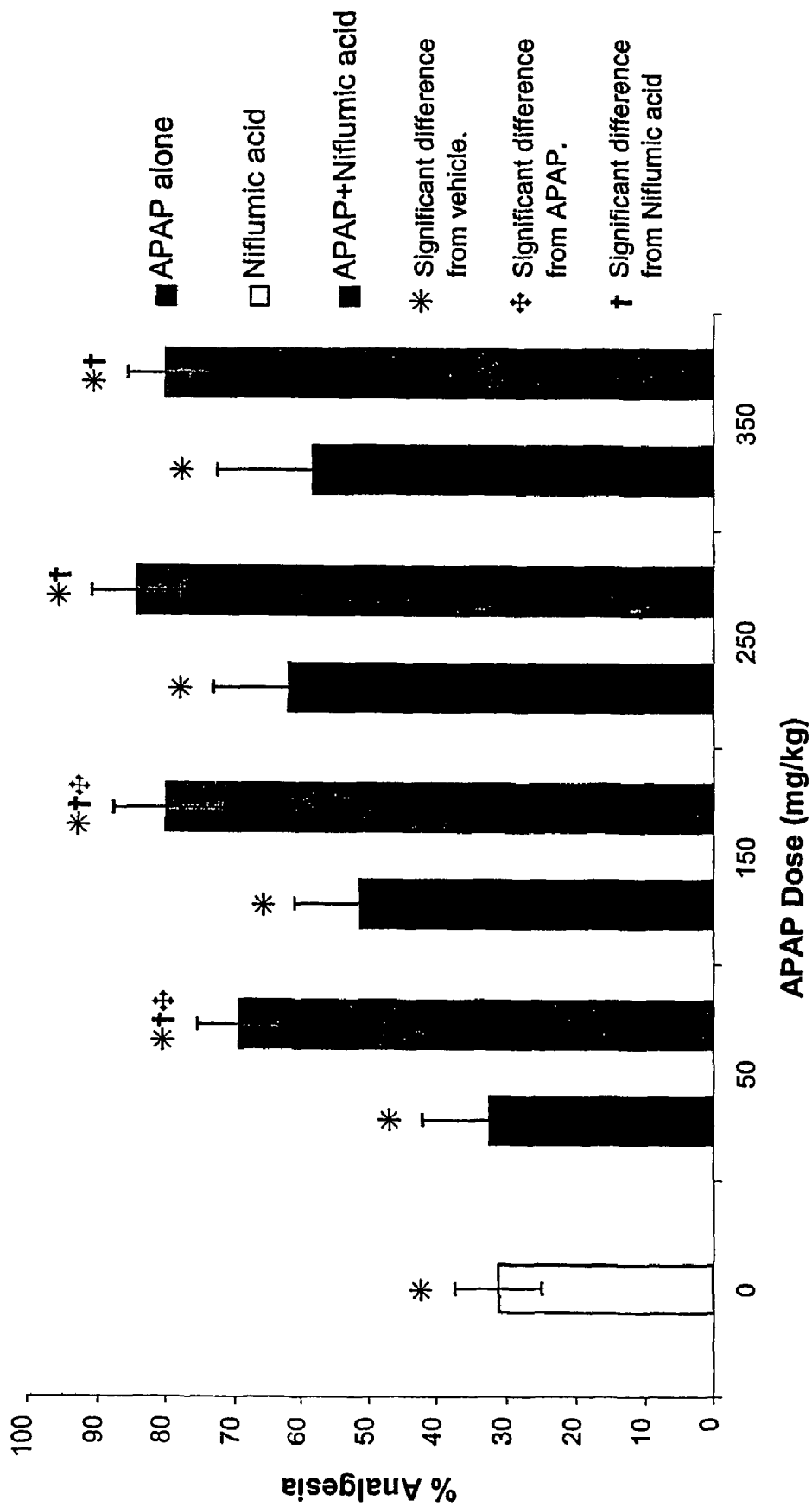
Fig. 1. The Effect of 62.5 mg/kg Niflumic acid on the Dose-response curve for APAP. Data represents mean % Analgesia +/- SEM (n=10).

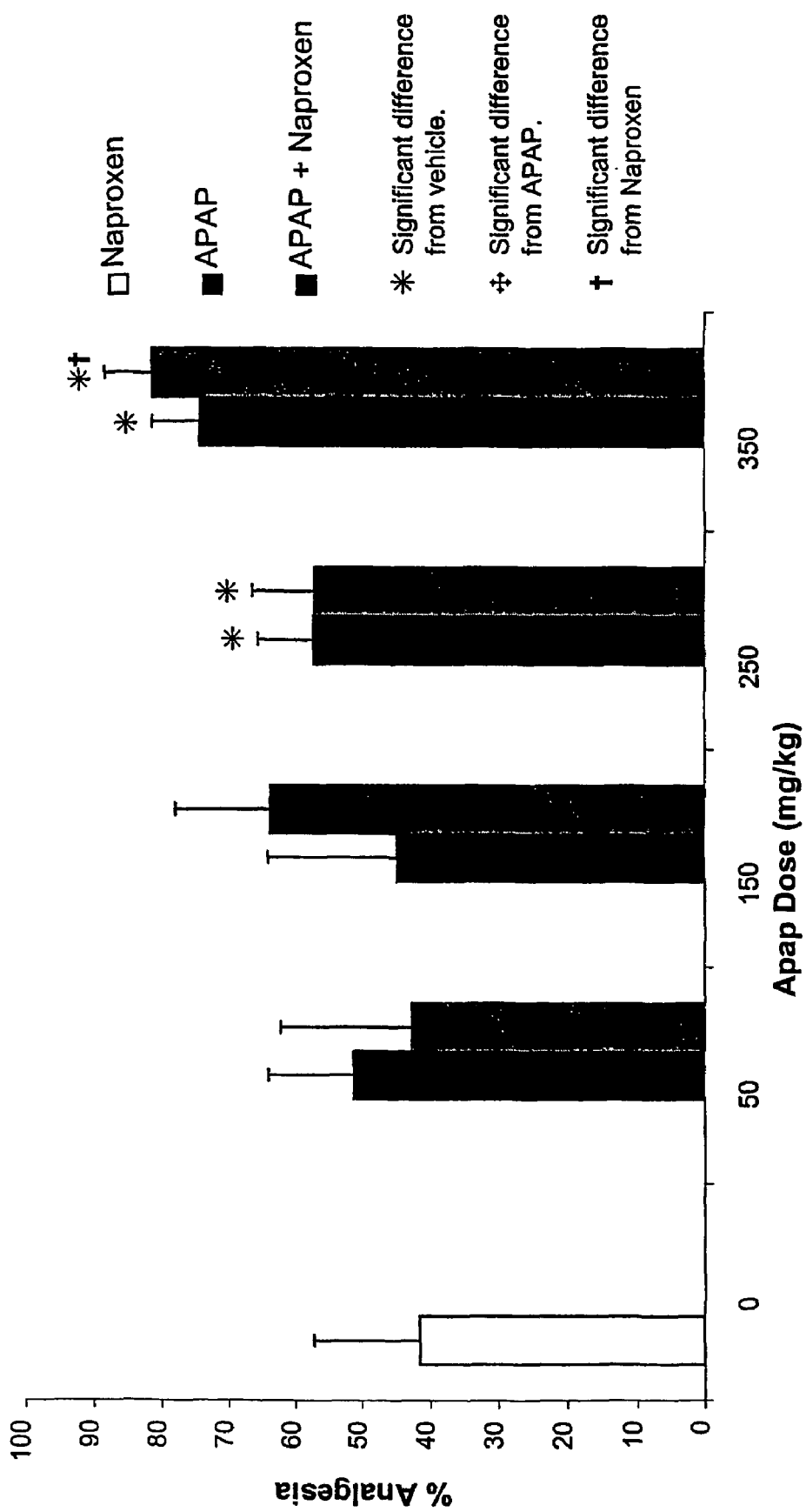
Fig. 2. The Effect of 15 mg/kg Naproxen on the Dose-response curve for APAP. Data represents Mean % Analgesia +/- SEM (n=10).

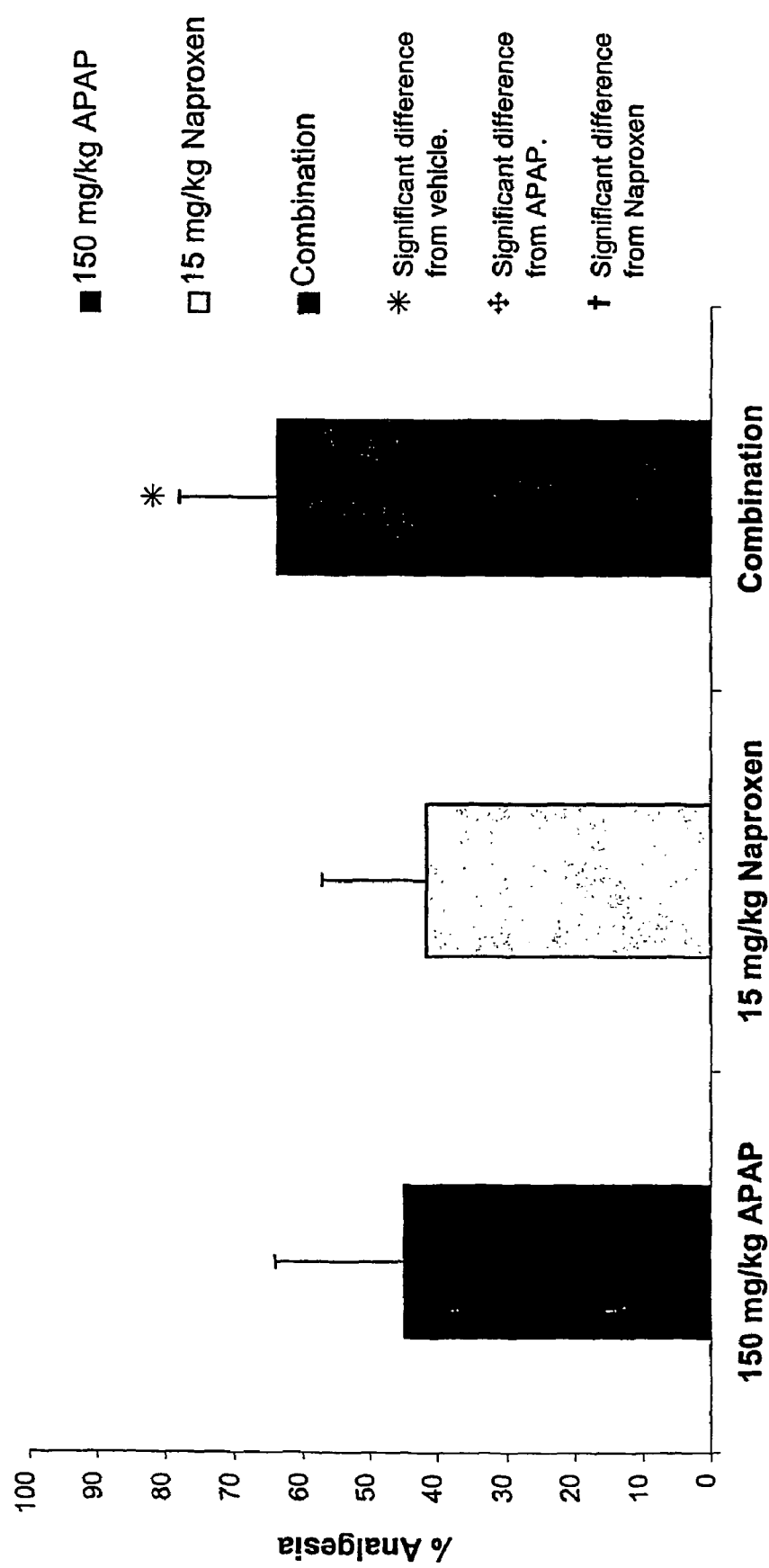
Fig. 3. The Effect of 15 mg/kg Naproxen on the Dose-response curve for APAP. Data represents Mean % Analgesia +/- SEM (n=10).

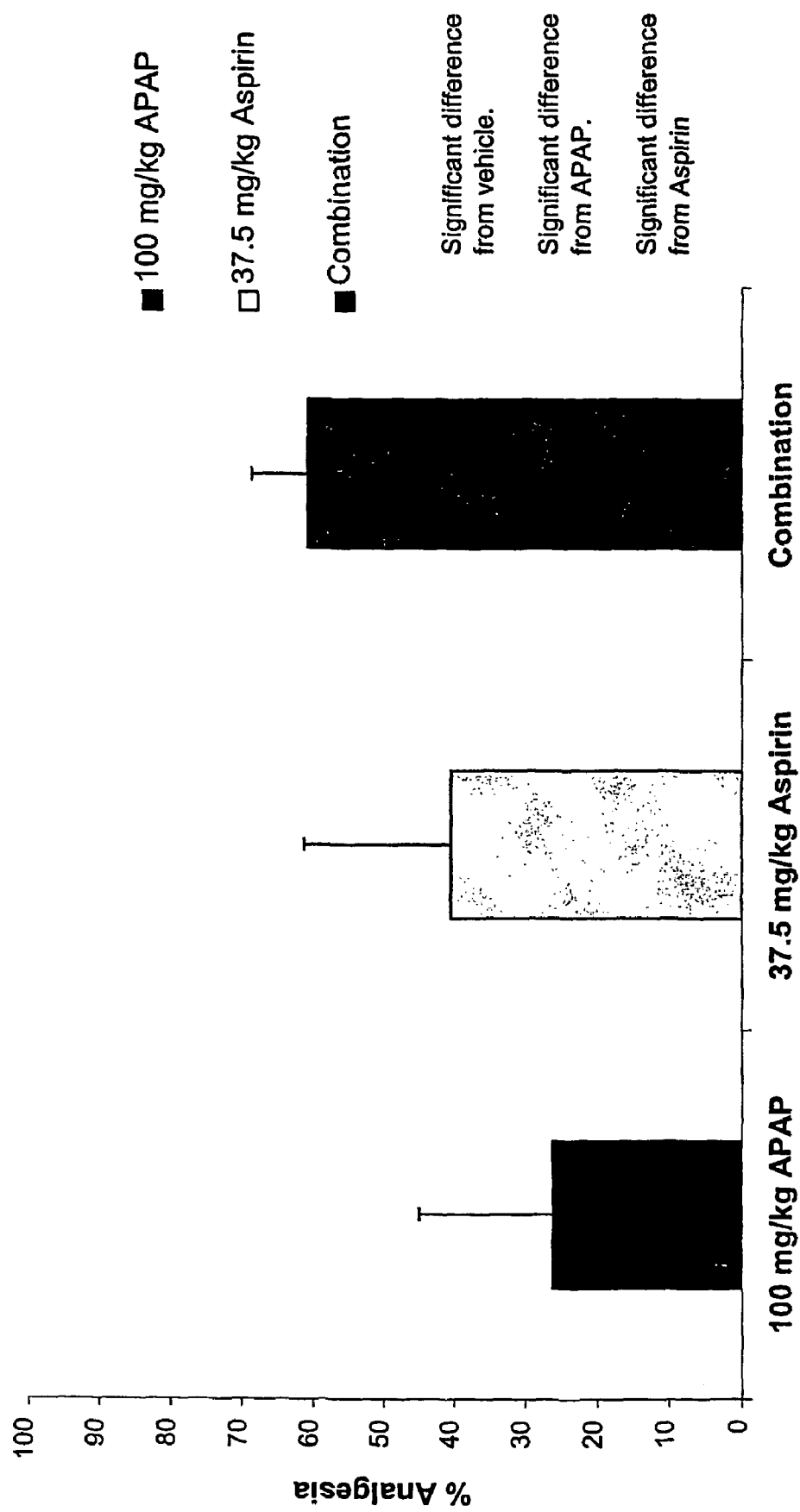
Fig. 4. The Effect of 37.5 mg/kg Aspirin on the Dose-response curve for APAP. Data represents Mean % Analgesia +/- SEM (n=10).

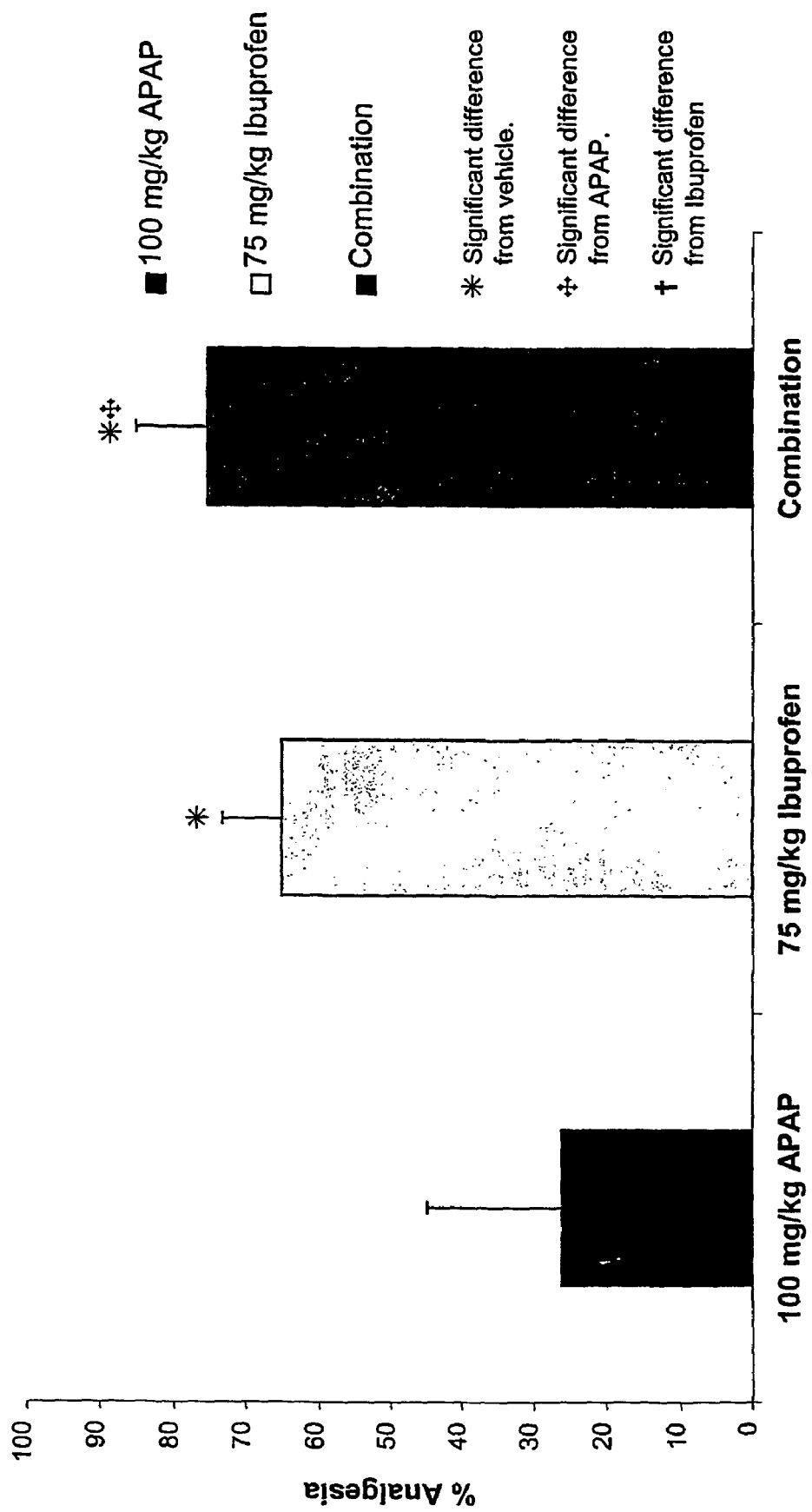
Fig. 5. The Effect of 75 mg/kg Ibuprofen on the Dose-response curve for APAP. Data represents Mean % Analgesia +/- SEM (n=10).

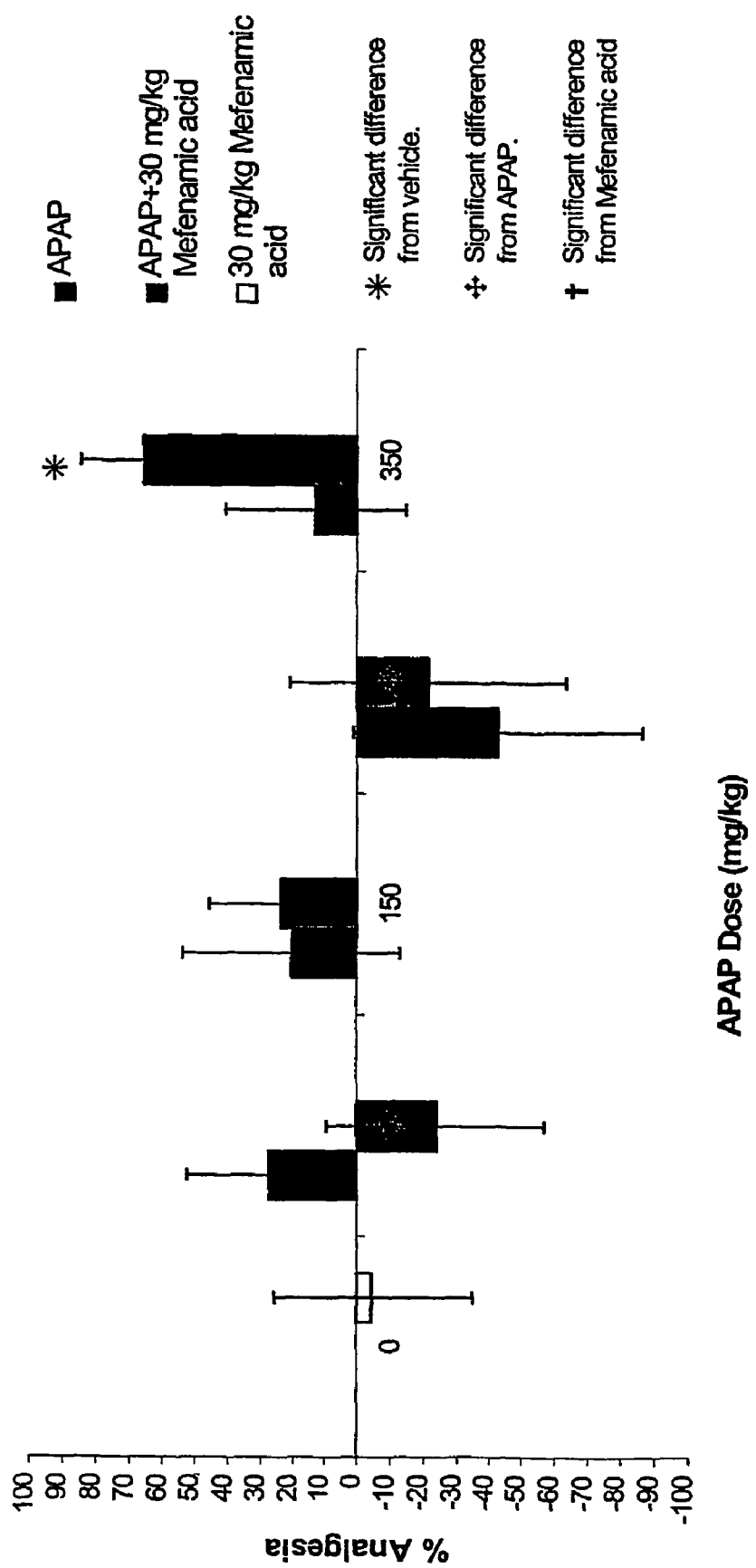
Fig. 6. The Effect of 30 mg/kg Mefenamic acid on the dose-response curve for APAP. Data represents mean % Analgesia +/- SEM (n=10).

PHARMACEUTICAL COMPOSITION COMPRISING PARACETAMOL AND NIFLUMIC ACID

This application is a 371 of PCT/EP01/03185 filed Mar. 20, 2001 which claims a benefit of UNITED KINGDOM 0006897.3 filed Mar. 23, 2000.

The present invention relates to pharmaceutical compositions containing N-acetyl-p-aminophenol, known by the generic names paracetamol, acetaminophen and APAP (hereinater referred to as paracetamol). In particular, the invention relates to a formulation comprising paracetamol in combination with niflumic acid.

Paracetamol is an analgesic and antipyretic agent which is widely used in prescription and non-prescription medicines, often in combination with other biologically active compounds including non-steroidal anti-inflammatory agents (NSAIDs) such as aspirin, ibuprofen, mefenamic acid or naproxen.

Niflumic acid is a known NSAID, however there has been no suggestion to co-administer it with paracetamol.

It has now been found that a combination of niflumic acid with paracetamol is surprisingly able to increase the maximum analgesic effect of paracetamol in an established model of pain. This advantageous effect is not obtained by using alternative NSAMDs such as aspirin, ibuprofen, mefenamic acid or naproxen.

Accordingly, in a first aspect, the present invention provides a pharmaceutical composition comprising an effective amount of paracetamol and an effective amount of niflumic acid or a pharmaceutically acceptable salt or ester thereof and a pharmaceutically acceptable excipient.

The paracetamol and niflumic acid or a pharmaceutically acceptable salt or ester thereof may be presented in separate unit dose compositions which are suitably adapted for concurrent administration (ie within about 5 minutes of each other) and preferably for simultaneous administration (ie at the same time).

More conveniently the paracetamol and niflumic acid or a pharmaceutically acceptable salt or ester thereof are presented together in the same unit dose composition, which has the advantage of simplifying the dosage regimen and improving patient compliance.

The compositions of this invention are usually adapted for oral administration, but formulations for parenteral or rectal administration, or topically applied formulations are also within the scope of this invention.

The composition is usually presented as a unit dose composition containing from 10 to 1000 mg of paracetamol and from 5 to 500 mg of niflumic acid or a pharmaceutically acceptable salt or ester thereof, more usually from 100 to 800 mg of paracetamol, for example 200 to 600 mg of paracetamol, and from 20 to 400 mg of niflumic acid or a pharmaceutically acceptable salt or ester thereof, for example from 40 to 300 mg of niflumic acid or a pharmaceutically acceptable salt or ester thereof. Most preferably unit doses contain from 300 to 500 mg of paracetamol and from 50 to 250 mg of niflumic acid or a pharmaceutically acceptable salt or ester thereof.

Such a composition is normally taken from 1 to 6 times daily, for example 2, 3 or 4 times daily so that the total daily amount administered to a patient in need therefore is up to 4000 mg of paracetamol and up to 1000 mg of niflumic acid or a pharmaceutically acceptable salt or ester thereof.

Examples of salts of niflumic acid include alkali metal salts thereof, such as the sodium or potassium salts or amino acid salts thereof, such as lysine or arginine salts.

A suitable ester of niflumic acid is the 2-morpholinoethyl ester, known as morniflumate.

In view of the advantageous interaction between paracetamol and niflumic acid or a pharmaceutically acceptable salt or ester thereof, a lower dose of paracetamol than those conventionally used, can be administered to obtain the same level of pain relief. This has the advantage that it may reduce the potential for patients to suffer toxic effects of paracetamol overdose, which can have fatal consequences or, at the very least, lead to irreversible liver damage.

Alternatively, a conventional dose of paracetamol in combination with a dose of niflumic acid or a pharmaceutically acceptable salt or ester thereof which is normally considered sub-therapeutic can be administered, thus reducing the side effects normally associated with NSAIDs.

Alternatively, a more conventional dose of paracetamol in combination with niflumic acid or a pharmaceutically acceptable salt or ester thereof, can afford a "power analgesic" able to alleviate more severe forms of acute pain.

The compositions of the present invention, therefore, have useful analgesic properties and may be used in the treatment of mild to moderate pain, or when acting as a "power analgesic" to treat more acute forms of pain, including migraine.

The compositions of the present invention also have useful anti-inflammatory properties.

Preferred dosage forms for oral administration includes tablets and capsules.

Preferred dosage forms for topical application include creams and ointments to be applied to the skin.

Preferred dosage forms for rectal application include suppositories.

Suitable excipients for use in this invention include lubricants, for example magnesium stearate and stearic acid; disintegrants, for example cellulose derivatives; starches; binders, for example modified starches and cellulose derivatives; glidants, for example colloidol silicas; compression aids, for example cellulose derivatives; as well as preservatives, suspending agents, wetting agents, flavouring agents, bulking agents, adhesives, colouring agents, sweetening agents appropriate to their form. Examples of such excipients are described in the *Handbook of Pharmaceutical Excipients* (Second Edition, 1994, edited by A. Wade and P. Weller, published by the American Pharmaceutical Association and the Pharmaceutical Press).

In addition to paracetamol, niflumic acid or a pharmaceutically acceptable salt or ester thereof and a pharmaceutically acceptable excipient, formulations of the invention may also contain other pharmaceutically active agents, for example other analgesics, anti-inflammatory analgesic agents, decongestants, antihistamines, antitussive agents, etc. Formulations may also contain a pharmaceutically acceptable analgesic adjuvant, for example caffeine.

The invention also provides a process for the preparation of a composition of the invention, which process comprises the admixture of paracetamol and niflumic acid or a pharmaceutically acceptable salt or ester thereof together with any pharmaceutically acceptable excipients, additional pharmaceutically acceptable active agents or adjuvants. Thus the paracetamol and niflumic acid or a pharmaceutically acceptable salt or ester thereof may be mixed together with one or more binders and granulated using water. The resulting granule may then be dried, sieved and mixed with additional excipients such as a lubricant and disintegrant before being compressed into tablets. Alternatively, the niflumic acid or a pharmaceutically acceptable salt or ester thereof may be omitted from the granulation step and subsequently added with the other excipients. In an alternative process, tablets may be prepared using direct compression grades of paracetamol including commercially available forms which obviates the need for a granulation step. Tablets may also be prepared by other processes known in the art such as by shaping of an extruded mixture. For capsule production, the paracetamol and niflumic acid or a pharmaceutically acceptable salt or ester thereof may be mixed and granulated as for tablet production and filled into suitably sized capsule shells to the desired fill weight.

The following Examples illustrate the present invention.

BRIEF DESCRIPTION OF THE DRAWINGS

FIG. 1 shows the effect of 62.5 mg/kg niflumic acid on the dose-response curve for APAP.

FIGS. 2–3 show the effect of 15 mg/kg naproxen on the dose-response curve for APAP.

FIG. 4 shows the effect of 37.5 mg/kg aspirin on the dose-response curve for APAP.

FIG. 5 shows the effect of 75 mg/kg ibuprofen on the dose-response curve for APAP.

FIG. 6 shows the effect of 30 mg/kg mefenamic acid on the dose-response curve for APAP.

EXAMPLE 1

The P-Phenyl-Quinone Induced Mouse Abdominal Constriction (MAC) Assay

The method is based on that described by Siegmund, Cadmus and Lu in "A Method for Evaluating both Non-Narcotic and Narcotic Analgesics" Proc. Soc. Exp. Biol. Med., 95: 729–731 (1957)).

DBA/2 mice were housed 20 per cage in a temperature and humidity controlled environment on a 12:12 hour light-dark cycle for five days with food and water ad libitum before testing. A range of doses of Paracetamol (APAP) were tested alone and in combination with niflumic acid, aspirin, ibuprofen, mefenamic acid and naproxen. Ten animals were randomly allocated to each drug group and experimental designs were used that allowed complete randomisation of the testing of drug groups. Drugs were suspended in 1% methylcellulose and administered 10 ml/kg po, 60 mins pre-test. Abdominal constriction was induced by i.p. injection of 10 ml/kg P-phenyl-quinone (0.025% in 5% ethanol/water) and the total number of constrictions in a twenty minute period were measured. A constriction is defined as a flattening of the abdomen with extension of the hind limbs. Testing was blind with one experimenter observing five animals. All experiments were performed in accordance with the Animals (Scientific Procedures) Act 1986 and subject to local ethical committee approval.

Analysis

For each drug group, the mean % inhibition of constrictions was calculated ((1-(test/control))*100) and appropriate statistics were performed on log-transformed data to test significant differences from vehicle and, in the case of groups receiving drug combinations, each drug alone.

Results

Results are summarised in FIGS. 1 to 6.

At all doses of paracetamol, addition of 62.5 mg/kg niflumic acid increased the % inhibition of constrictions beyond the maximum effect of paracetamol alone. (FIG. 1)

This effect was a significant improvement on vehicle and either drug alone in the groups that received combinations of (i) 50 mg/kg Paracetamol+62.5 mg/kg Niflumic acid and (ii) 150 mg/kg Paracetamol+62.5 mg/kg Niflumic acid. At these doses, each drug alone had a small but significant effect.

This effect was not seen with naproxen and aspirin at doses with a similar efficacy to 62.5 mg/kg Niflumic acid (15 mg/kg and 37.5 mg/kg respectively) (FIGS. 2–4)

The analgesic effect of ibuprofen (75 mg/kg) in combination with APAP (100 mg/kg) was not significantly greater than the effect of 75 mg/kg ibuprofen alone, suggesting there is no additive interaction between these two drugs (FIG. 5)

The analgesic effect of a combination of 30 mg/kg mefenamic acid with a range of doses of APAP did not elicit a significant advantage over APAP alone. (FIG. 6)

EXAMPLE 2

A typical tablet of the invention can be prepared as follows:

| INGREDIENT | mg/tablet | g/batch |
|---|---|---|
| 1. Paracetamol | 500 | 500 |
| 2. Niflumic acid | 90 | 90 |
| 3. PVP (polyvinylpyrrolidone) | 20 | 20 |
| 4. Ac di sol (Croscarmellose sodium) | 35 | 35 |
| 5. Magnesium stearate | 5 | 5 |

Method
a) Sieve items 1, 2 and 3 through 0.2 mm screen and in a suitable mixer
b) Add purified water and mix until a medium density granule has been achieved
c) Dry in a tray oven for 2 hours at 50 C.
d) Sieve the resulting granule through a 0.5 mm screen
e) Sieve items 4 and 5 through a 0.2 mm screen and add to the granulate from step d)
f) Blend the mixture from step e) for 5 minutes using a suitable mixer
e) Compress the mixture from step f) using a suitable tablet press to produce tablets with a target weight of 650 mg with each tablet containing approximately 500 mg of paracetamol and 90 mg of niflumic acid.

The invention claimed is:

1. A pharmaceutical composition for oral administration comprising 50 mg/kg paracetamol and 62.5 mg/kg niflumic acid or a pharmaceutically acceptable salt or ester thereof, and a pharmaceutically acceptable excipient wherein said composition is prepared in an oral dosage form.

2. A composition according to claim 1 in the form of a tablet or capsule.

* * * * *